United States Patent [19]

Green

[11] 4,402,445

[45] Sep. 6, 1983

[54] SURGICAL FASTENER AND MEANS FOR APPLYING SAME

[75] Inventor: David T. Green, Norwalk, Conn.

[73] Assignee: United States Surgical Corporation, Norwalk, Conn.

[21] Appl. No.: 310,065

[22] Filed: Oct. 9, 1981

[51] Int. Cl.³ .......................................... A61B 17/04
[52] U.S. Cl. ................................. 227/19; 24/211 R; 227/15; 227/67; 227/70; 227/71; 227/76; 227/77; 227/152; 227/DIG. 1; 128/334 R; 128/334 L; 339/128; 339/91 R
[58] Field of Search ................. 24/221 R; 128/303 A, 128/325, 329, 330, 334 R, 334 C; 227/19, 15, 16, 17, 18, 67, 70, 71, 76, 77, 152, 144, DIG. 1; 339/91 R, 128; 402/61, 64, 65, 80 P; 411/457, 471, 472, 473

[56] References Cited

U.S. PATENT DOCUMENTS

| | | | |
|---|---|---|---|
| 1,452,373 | 4/1923 | Gomez | 227/18 |
| 2,453,056 | 11/1948 | Zack | 128/334 |
| 2,881,762 | 4/1959 | Lowrie | 128/337 |
| 3,069,962 | 12/1962 | Rapata | 85/8.8 |
| 3,093,027 | 6/1963 | Rapata | 85/5 |
| 3,166,072 | 1/1965 | Sullivan | 128/334 |
| 3,220,078 | 11/1965 | Preziosi | 402/80 P |
| 3,254,650 | 6/1966 | Collito | 128/334 |
| 3,378,812 | 4/1968 | Fitzgerald | 339/128 |
| 3,512,289 | 5/1970 | Hayes | 128/330 X |
| 3,570,497 | 3/1971 | Lemole | 128/335.5 |
| 3,571,864 | 3/1971 | Oger | 24/221 R |
| 3,595,201 | 7/1971 | Oudenhoven | 116/114 |
| 3,641,804 | 2/1972 | Oudenhoven | 72/409 |
| 4,006,747 | 2/1977 | Kronenthal et al. | 128/335 |
| 4,060,089 | 11/1977 | Noiles | 128/325 |
| 4,147,168 | 4/1979 | Hayes et al. | 128/329 R X |
| 4,195,635 | 4/1980 | Ritchey | 128/330 |
| 4,260,210 | 4/1981 | Babuka et al. | 339/91 R |
| 4,305,539 | 12/1981 | Korolkov et al. | 227/19 X |

FOREIGN PATENT DOCUMENTS 972731 10/1964 United Kingdom .

*Primary Examiner*—Paul A. Bell
*Attorney, Agent, or Firm*—Robert R. Jackson; John E. Nathan

[57] ABSTRACT

A surgical fastener of plastic or plastic-like material includes initially separate fastener and retainer members. The fastener member has at least two parallel prongs, each of which fits into a respective one of at least two apertures in the retainer member. The prongs twist as they enter the apertures. Then the prongs return to their initial orientation in which they interlock with the retainer member to form a finished fastener. The fastener is applied by forcing the fastener member prongs through the tissue to be fastened with the aid of metal pins contiguous with each prong. The pins are automatically withdrawn from the tissue after the prongs interlock with the retainer member and before the fastened tissue is removed from the fastener applying apparatus.

23 Claims, 22 Drawing Figures

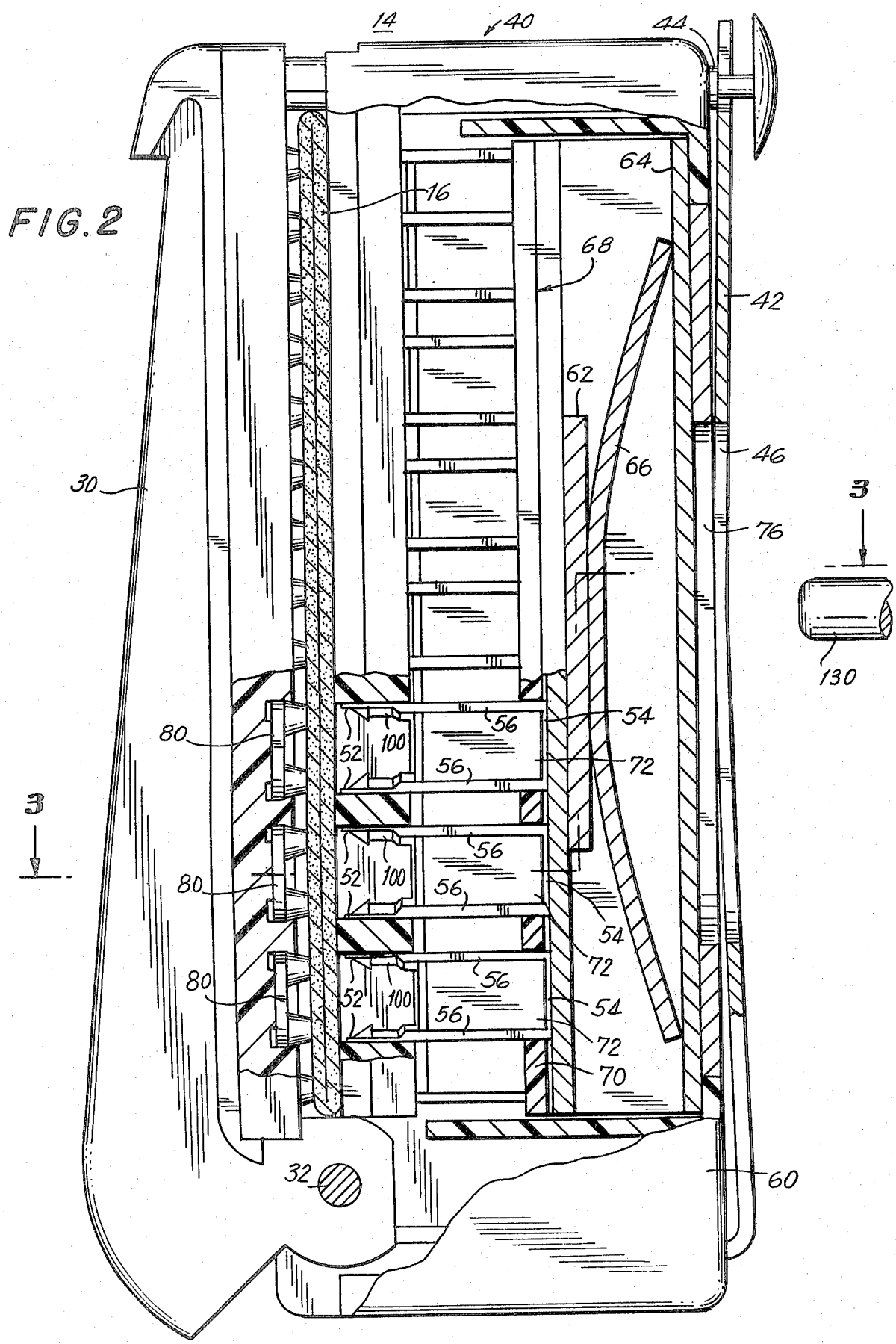

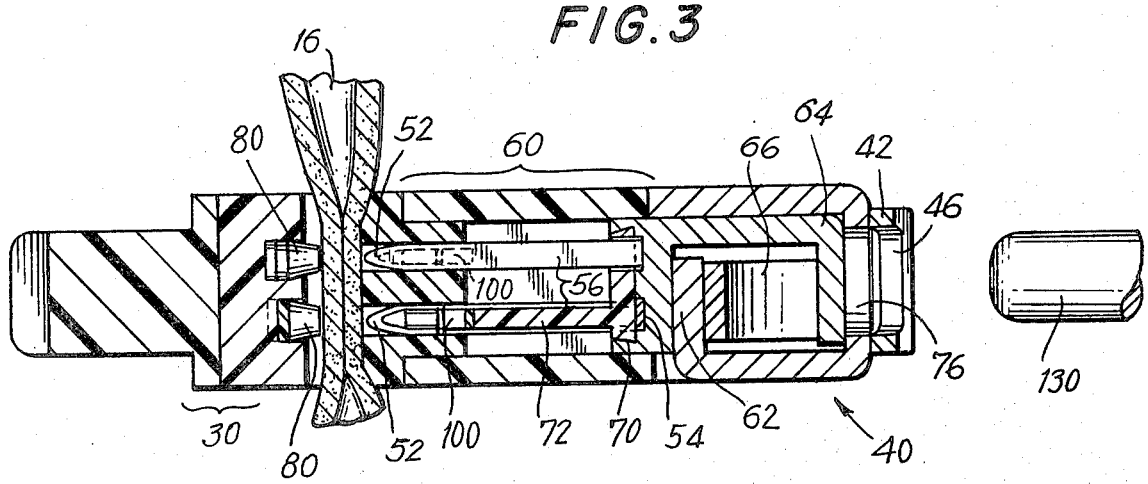

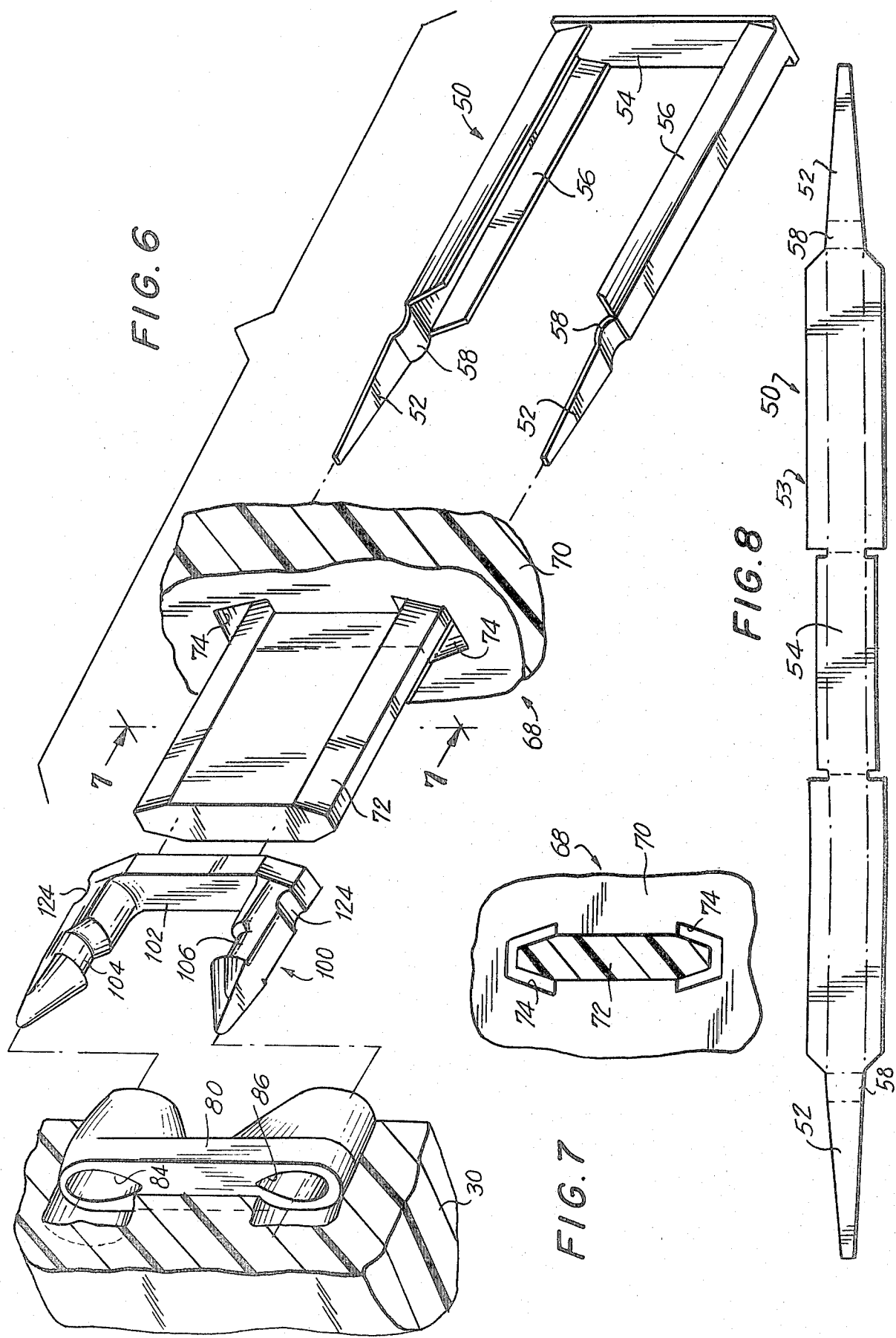

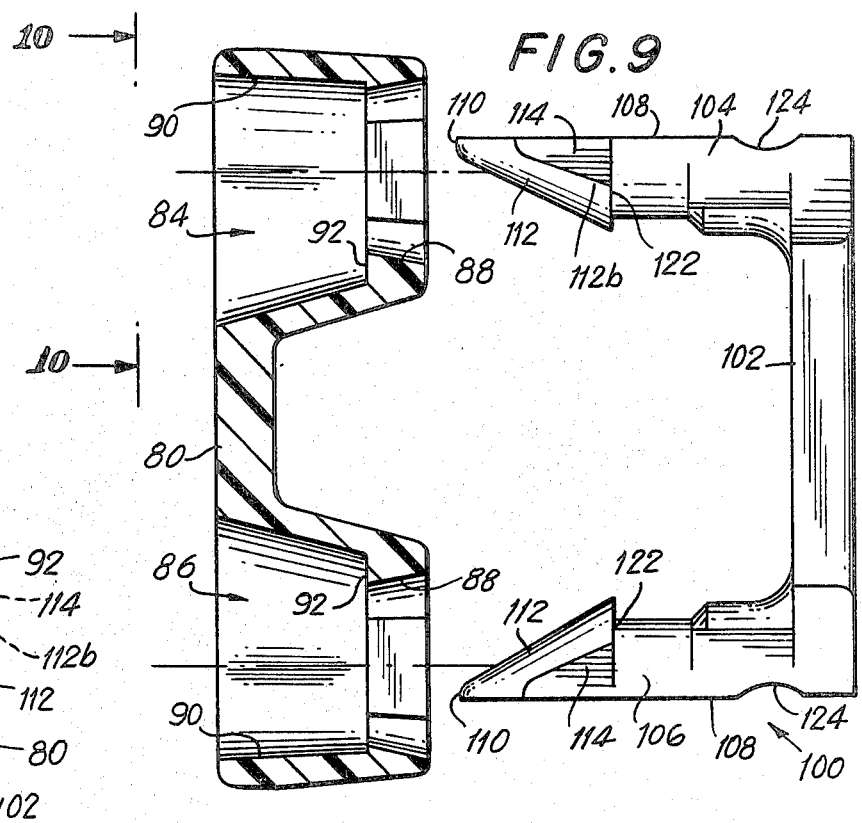
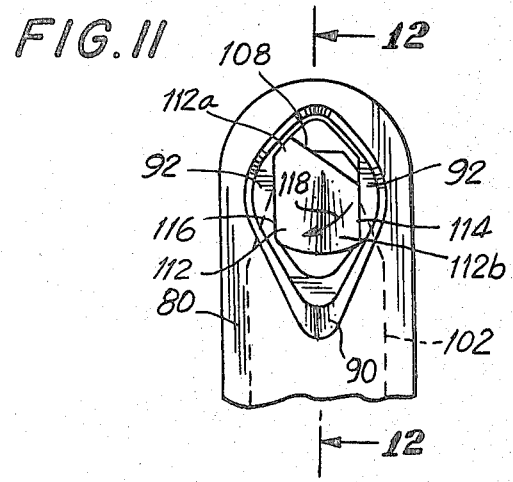
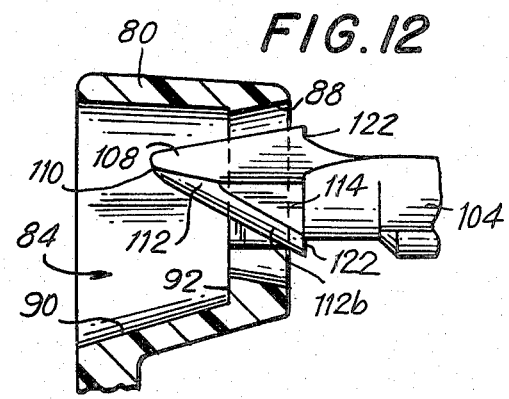
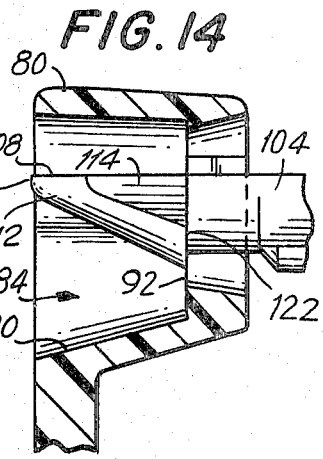
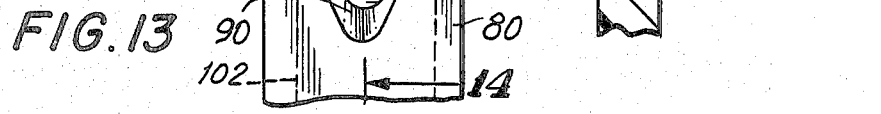

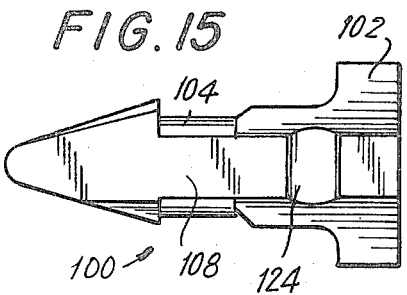
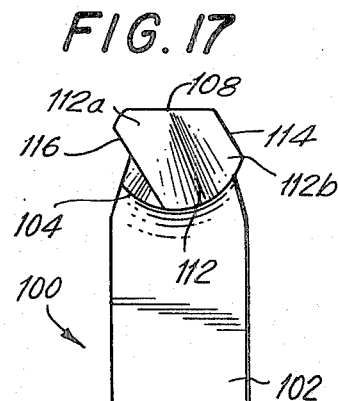
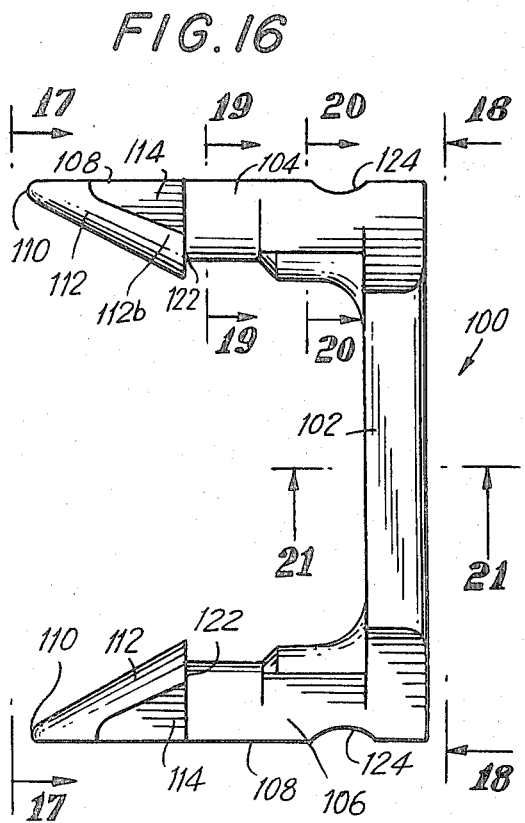
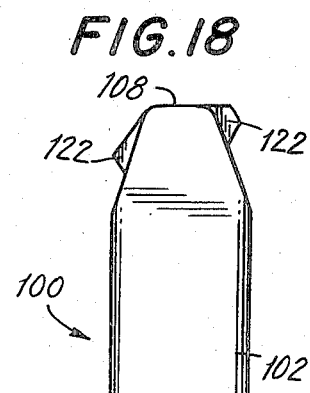
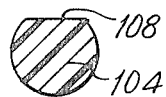
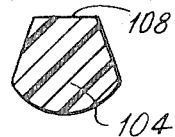
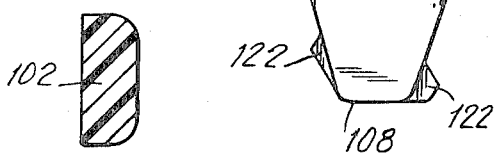

SURGICAL FASTENER AND MEANS FOR APPLYING SAME

BACKGROUND OF THE INVENTION

This invention relates to surgical fastener apparatus, and more particularly to surgical fasteners of plastic or plastic-like materials. The invention also relates to apparatus for applying such surgical fasteners to body tissue.

Surgical stapling has been developed to avoid the difficulty of applying individual sutures of thread, gut, wire, or the like. Surgical stapling devices allow the surgeon to fasten body tissue by applying surgical staples singly in succession or simultaneously in parallel, depending on the stapling instrument. The surgical staples are typically metal wire which is usually an inert material such as tantalum or stainless steel, although metals such as magnesium which are gradually absorbed by the body are also known.

In some surgical procedures it is desirable to use non-metallic sutures. For example, it is possible for the presence of metal staples in the body to scatter X rays and thereby degrade the quality of a radiograph. And in some cases metal staples may migrate undesirably in the body during the months or years following the surgery. For these and other reasons it may be desirable to use non-metallic suture materials such as natural or synthetic polymers or resins or collagen which do not impede the transmission of X rays, and which may also be absorbed relatively rapidly by the body. For convenience herein and in the appended claims, all such non-metallic suture materials which are suitable for use in the practice of the present invention will be referred to as "plastic-like materials". To be suitable for use in the present invention, the suture material must be relatively flexible and elastic, and the term "plastic-like materials" as used herein is therefore limited to such materials. However, this term is not limited with respect to biological absorbability, and the "plastic-like materials" referred to herein may therefore be either absorbable or non-absorbable.

The plastic-like materials mentioned above generally have physical properties which are substantially different from the physical properties of metal. These plastic-like materials generally do not lend themselves to substitution for the metal wire in surgical stapling apparatus because fastener structures of these materials are usually not strong enough or rigid enough to pierce or penetrate the tissue to be fastened. Fastener structures of these materials also cannot be bent or crimped during application in the same way that metal staples can be bent or crimped. These materials are generally too flexible to hold a finished staple shape.

It is therefore an object of this invention to provide improved surgical fastening apparatus.

It is a more particular object of this invention to provide improved surgical fasteners of plastic-like materials, and also to provide improved apparatus for applying such fasteners.

SUMMARY OF THE INVENTION

These and other objects of the invention are accomplished in accordance with the principles of the invention by providing surgical fasteners comprising initially separate but interlockable fastener members and retainer members, both members being of plastic-like material. The fastener members have a base and at least two spaced substantially parallel prongs perpendicular to the base. The retainer members have an aperture associated with each prong of the associated fastener member. The free end of each prong is adapted to be received in and to interlock with the associated retainer member aperture. The free end portion of each prong and the interior surface of each retainer member aperture have cam surface portions which cooperate to cause the prong to twist about its longitudinal axis as the prong enters the aperture. This allows the interlocking surface portions of the prong and the aperture to bypass one another, after which the cooperating cam surface portions disengage and allow the prong to twist back to its initial alignment in which the interlocking surface portions hold the fastener member and retainer member together.

The apparatus for applying the surgical fasteners of this invention comprises retainer member support means located on one side of the body tissue to be fastened and initially containing at least one retainer member, and a fastener member holding assembly located on the other side of the body tissue and initially containing a fastener member aligned with each retainer member. The fastener member holding assembly includes a sharply pointed metal pin parallel to and contiguous with each fastener member prong, the sharply pointed end of each pin extending beyond the free end of the associated prong. The fastener member holding assembly also includes means for driving the pins and the fastener member toward the associated retainer member in the retainer member support means so that the pins and the prongs pierce and pass through the tissue to be fastened and the ends of the prongs enter and interlock with the apertures in the retainer member. The pins facilitate the passage of the prongs through the tissue. The fastener member holding assembly further includes means for automatically retracting the pins after the two parts of the fastener are interlocked. This pin retracting means is preferably automatic to insure that the pins are retracted before the fastened tissue can be removed from the fastener applying apparatus.

Further features of the invention, its nature and various advantages will be more apparent from the accompanying drawing and the following detailed description of the invention.

BRIEF DESCRIPTION OF THE DRAWING

FIGS. 1a and 1b are sometimes referred to collectively as FIG. 1.

FIG. 2 is a partly sectional elevational view of a portion of the apparatus of FIG. 1 taken along the line 2—2 in FIG. 1b and shows that apparatus prior to fastening of the tissue.

FIG. 3 is a sectional view taken along the line 3—3 in FIG. 2.

FIG. 5 is a sectional view taken along the line 5—5 in FIG. 4.

FIG. 6 is an exploded perspective view of a portion of the apparatus of FIGS. 1-5.

FIG. 7 is a sectional view taken along the line 7—7 in FIG. 6.

FIG. 8 is a plan view of a blank for making one of the parts shown in detail in FIG. 6.

FIG. 9 is an elevational view, partly in section, of a surgical fastener of this invention.

FIG. 10 is a view taken along the line 10—10 in FIG. 9.

FIG. 11 is a view similar to FIG. 10 showing an intermediate stage in the mating of the two parts of the fastener.

FIG. 12 is a sectional view taken along the line 12—12 in FIG. 11. The fastener prong in FIG. 12 is not in section.

FIG. 13 is a view similar to FIG. 11 showing the final stage in the mating of the two parts of the fastener.

FIG. 14 is a sectional view taken along the line 14—14 in FIG. 13. The fastener prong in FIG. 14 is not in section.

FIG. 15 is an end view of one part of the fastener of FIG. 9.

FIG. 16 is an elevational view of one part of the fastener of FIG. 9.

FIGS. 17 and 18 are views taken along the lines 17—17 and 18—18, respectively, in FIG. 16.

FIGS. 19, 20, and 21 are sectional views taken along the lines 19—19, 20—20, and 21—21, respectively, in FIG. 16.

DETAILED DESCRIPTION OF THE INVENTION

Figure 1A:
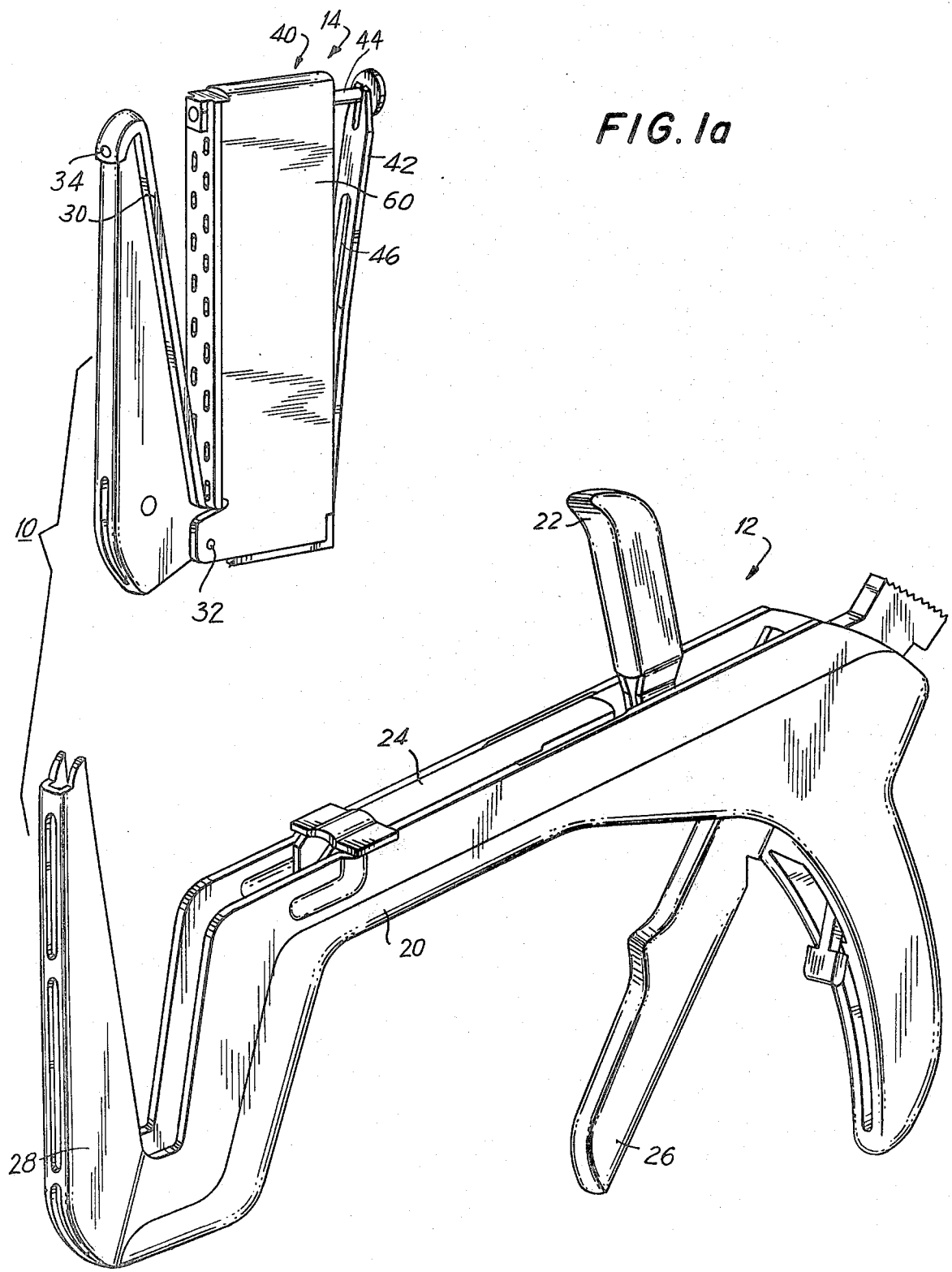
FIG. 1a is a perspective view of illustrative apparatus for applying the surgical fasteners of this invention and shows the fastener applying cartridge separate from the actuator assembly with which the cartridge is used.

The apparatus shown in FIG. 1 and referred to generally by the reference number 10 consists of two main parts. These are actuator assembly 12 and fastener applying cartridge 14. Actuator assembly 12 may be identical to the corresponding portion of the apparatus shown in commonly assigned, co-pending Green U.S. patent application Ser. No. 267,080, filed May 26, 1981. Actuator assembly 12 therefore forms no part of the present invention and will not be described in detail herein. Indeed, other actuator assemblies may be readily substituted for the actuator assembly shown. An example of another suitable actuator assembly is shown in commonly assigned, co-pending Green U.S. patent application Ser. No. 188,691, filed Sept. 29, 1980. Thus the particular actuator assembly shown in FIG. 1 illustrates only one possible environment of the invention and is not necessary to understanding or practicing the invention.

Actuator assembly 12 comprises a frame 20, a clamp actuating mechanism pivoting element 22 and associated reciprocating element 24, and pivoting pusher actuating member 26. Fastener applying cartridge 14 is removably mounted in the distal portion of frame 20 by means of a detent or other similar connection between distal frame leg 28 and fastener retainer support member 30.

As is best seen in FIGS. 2 and 3, fastener applying cartridge 14 includes longitudinal fastener retainer support member 30 and fastener holding assembly 40. Fastener holding assembly 40 is pivotally connected to member 30 by pin 32 adjacent one end of member 30. Retainer support member 30 contains a plurality of fastener retainer members 80 arranged in two parallel rows. Fastener holding assembly 40 similarly contains a plurality of fastener members 100 arranged in two parallel rows. When fastener holding assembly 40 is pivoted substantially parallel to retainer support member 30 as shown, for example, in FIG. 2, each fastener member 100 is opposite a respective one of retainer members 80. The fastener members and retainer members in each row are offset from the fastener members and retainer members in the other row to provide a staggered arrangement of finished fasteners in the fastened tissue.

Figure 1B:
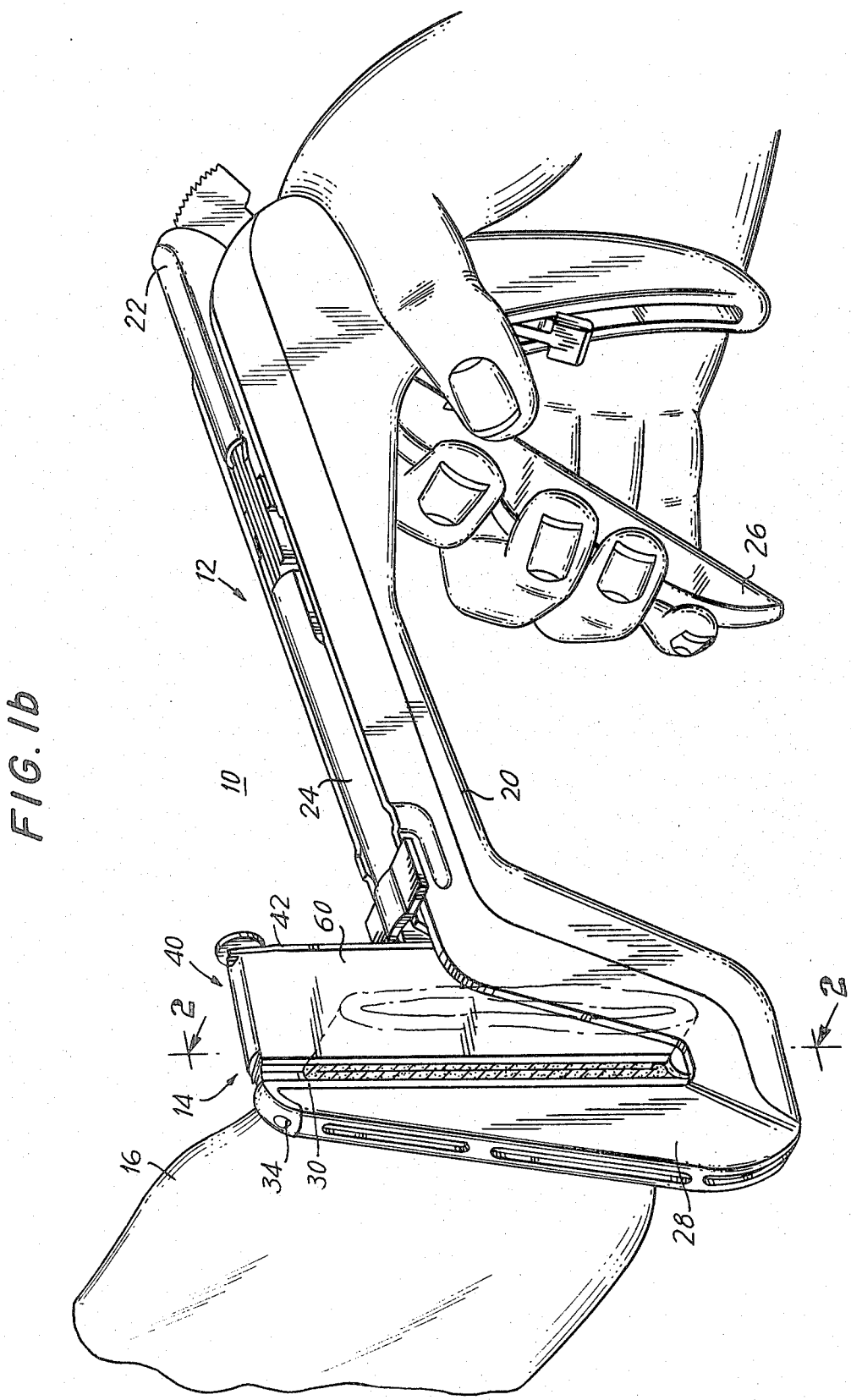
FIG. 1b is similar to FIG. 1a, but shows the fastener applying cartridge mounted in the actuator assembly and the apparatus ready to apply fasteners to body tissue.
Figure 4:
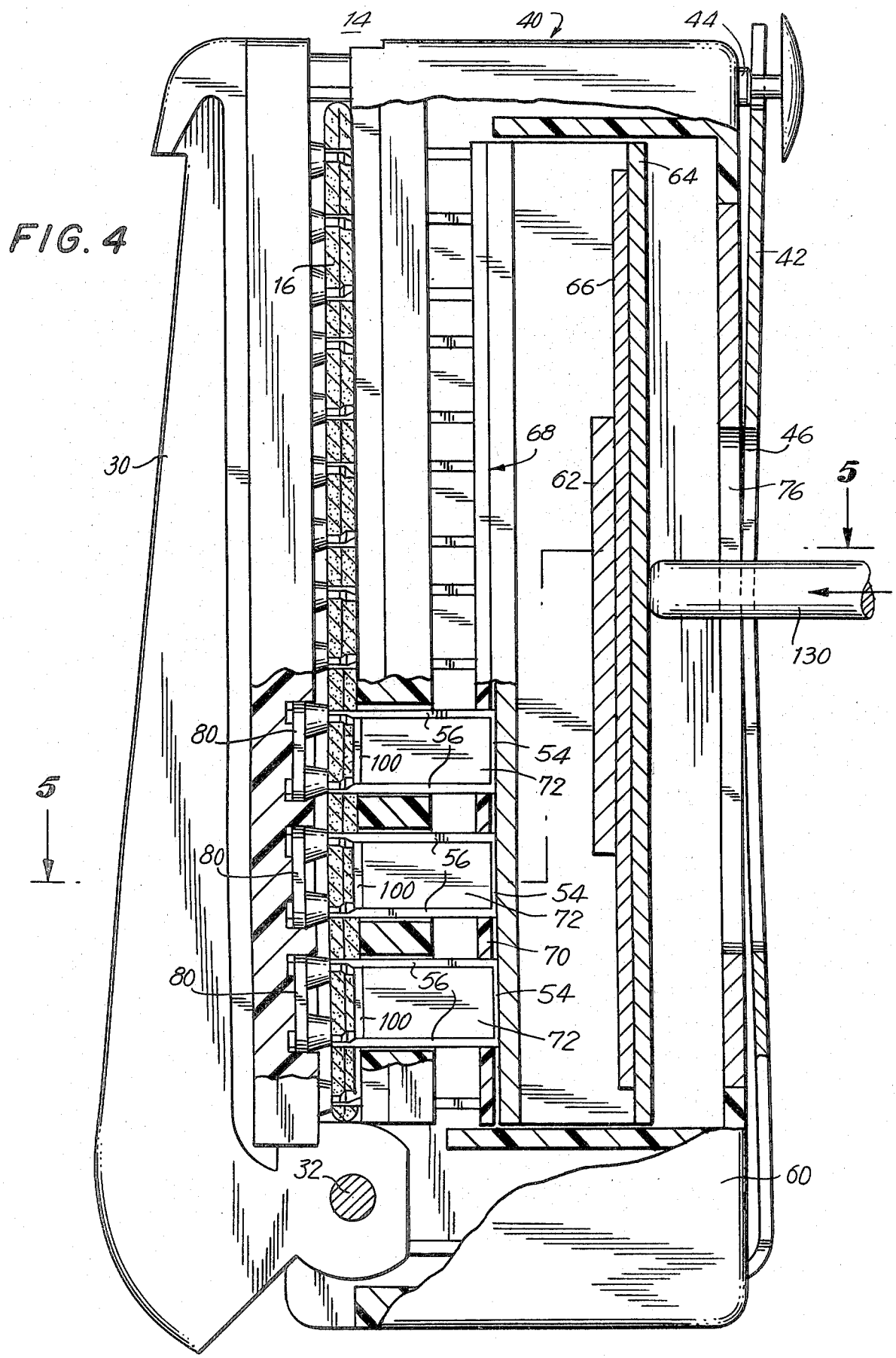
FIG. 4 is a view similar to FIG. 2 but shows the apparatus after the tissue has been fastened.

The apparatus of FIG. 1 is used to fasten body tissue as follows. Pivoting clamp actuating element 22 is pivoted up out of frame 20 to proximally retract reciprocating clamp actuating element 24 as shown in FIG. 1a. A fastener applying cartridge 14 is inserted in frame 20. With element 24 proximally retracted, fastener holding assembly 40 can pivot away from retainer support member 30 as also shown in FIG. 1a. With cartridge 14 thus open, the tissue 16 to be fastened is placed between the opposing faces of cartridge elements 30 and 40. Pivoting clamp actuating element 22 is then pivoted parallel to frame 20 to distally extend clamp actuating element 24 as shown in FIG. 1b. The distal end of element 24 contacts the proximal side of fastener holding assembly 40 and pivots it toward retainer support member 30 to clamp the tissue to be fastened between the opposing faces of elements 30 and 40. When fastener holding assembly 40 is substantially parallel to retainer support member 30, the tissue is fully clamped and ready to be fastened. This condition of fastener applying cartridge 14 is best seen in FIGS. 2 and 3. Pivoting pusher actuating member 26 is then pivoted toward the butt of frame 20 to actuate fastener holding assembly 40 to drive fastener members 100 from assembly 40, through the tissue, and into interlocking engagement with retainer members 80 as shown in FIGS. 4 and 5. Fastening of the tissue is now complete and the fastened tissue can be removed from the apparatus. Pivoting pusher actuating member 26 is released and returns to its initial position. Pivoting clamp actuating member 22 is pivoted out of frame 20 to retract reciprocating clamp actuating member 24. This allows fastener holding assembly 40 to pivot away from retainer support member 30 so that the apparatus can be removed from the fastened tissue. Retainer members 80 pull out of member 30 and remain interlocked with fastener members 100 to secure the tissue. Expended fastener applying cartridge 14 is removed from frame 20 and discarded. A new cartridge is loaded in the frame when additional tissue fastening is required.

The surgical fasteners of this invention are best seen in detail in FIGS. 6 and 9–21. Each fastener includes a retainer member 80 and an initially separate fastener member 100. Each fastener member 100 has a longitudinal base 102 and at least two substantially parallel prongs 104, 106 extending substantially perpendicularly from the base at spaced locations along the length of the base. At least two prongs are required on each fastener member because each prong twists about its longitudinal axis during mating with the associated retainer member 80, and the presence of two or more prongs keeps base 102 parallel to the retainer member during twisting of the prongs (and also after the fastener is in place in the tissue). Although in the particular embodiment shown in the drawing each fastener member 100 has only two prongs, it will be apparent that more than two prongs could be employed if desired.

Each retainer member 80 is a longitudinal member substantially parallel to the base 102 of the associated fastener member 100. Each retainer member has at least two apertures 84, 86, each adapted for receiving the free end of a respective one of the prongs of the associated fastener member. At least two apertures are required in each retainer member 80 for the same reason that two prongs are required on each fastener member. The retainer member causes the fastener prongs to twist during mating with the retainer member, and two apertures are required so that the retainer member will remain parallel to the fastener member during this twisting of the prongs (and also after the fastener is in place in the tissue).

Fastener elements 80 and 100 are both made of plastic-like material as that term is defined above. As compared to the metal from which surgical staples are typically made, the plastic-like material of fastener elements 80 and 100 is relatively soft, flexible, and elastic. Accordingly, prongs 104 and 106 of fastener members 100 generally cannot, by themselves, penetrate the tissue to be fastened. To assist the fastener prongs to penetrate the tissue, staple holding assembly 40 includes a metal pin 52 (FIGS. 2 and 6) which is contiguous with each prong of each fastener member and which travels with the associated prong during the driving stroke of the apparatus. Each pin 52 extends a short distance beyond the free end of the associated prong and is sharply pointed to facilitate penetration of the tissue. The side 108 of each prong which is contiguous with the associated pin 52 conforms to the side surface of the pin so that the prong is at least partly supported by the pin. In the particular embodiment shown, side surface 108 is substantially flat. The remaining side surfaces (referred to collectively as the free side surface) of each prong are shaped to perform a variety of functions, all of which are described in detail below. The first of these functions is to facilitate passage of the prong through the tissue without the prong becoming separated from the associated pin 52. For this purpose, the free end of the prong comes to a point 110 which is contiguous with the side surface of the associated pin 52, and the adjacent portion 112 of the free side surface is inclined away from the associated pin 52 in the direction away from point 110. In the particular embodiment shown in the drawing, free side surface portion 112 is a fragment of a conical surface. Thus as prong 104 or 106 follows the associated pin 52 through the tissue, the pressure of the tissue on surface portion 112 tends to keep the prong contiguous with the pin.

Although pins 52 can be made in many ways, in the particular embodiment shown, each pin is the end of a U-shaped member 50 (best seen in FIG. 6) having a base 54 and two parallel channel-shaped portions 56 extending perpendicularly from opposite ends of the base. Each pin 52 extends from the free end of a respective one of channel portions 56. A flat blank 53 from which pin member 50 can be made is shown in FIG. 8.

After the prongs 104 and 106 of a fastener member 100 have passed through the tissue with the aid of pins 52, the free ends of the prongs enter retainer member apertures 84 and 86 and interlock with the retainer member as will now be described. Each of retainer member apertures 84 and 86 has a relatively small initial portion 88 and a relatively large final portion 90. Between initial and final portions 88 and 90 is an interlocking surface portion 92 which is substantially perpendicular to the longitudinal axis of the associated fastener member prong 104 or 106. Each of apertures 84 and 86 is substantially symmetrical about the plane defined by the central longitudinal axis of the retainer member and the longitudinal axes of the associated fastener member prongs. (This plane is referred to as the plane of symmetry of the retainer member apertures.) As is apparent from FIG. 10, the initial portion 88 of each retainer member aperture is too small to pass the free end of the associated fastener member prong without some twisting of the prong as described in detail below. As is apparent from FIG. 13, however, the final portion 90 of each aperture is large enough to receive the free end of the prong either twisted or untwisted.

As is best seen in FIGS. 9, 10, and 17, the otherwise conical free side surface 112 of each fastener member prong is cut away to produce two substantially flat surface portions 114 and 116 on respective opposite sides of the longitudinal axis of the prong. Flat surface portions 114 and 116 are substantially parallel to the longitudinal axis of the associated prong and to one another, but they are skewed or not parallel to the above-mentioned plane of symmetry of the associated retainer aperture 84 or 86. Although the initial portion 88 of each retainer aperture is too small to pass the free end of the associated prong in the initial angular orientation of the prong, the free end of the prong can pass through initial aperture portion 88 when the prong is twisted about its longitudinal axis so that flat surface portions 114 and 116 are substantially parallel to the above-mentioned plane of symmetry of the retainer member apertures. This is apparent from FIG. 11 which shows the end of a prong twisted for passage through the initial portion 88 of a retainer member aperture. Appropriate twisting of the prongs is accomplished automatically as will now be described.

As can be seen, for example, in FIG. 10, the location and angle of flat surface portion 116 is such that a portion 112a of conical surface portion 112 remains between flat surface portions 108 and 116. No comparable portion of conical surface portion 112 remains between flat surface portions 108 and 114 because these two flat surface portions are contiguous. On the other hand, there is a portion 112b of conical surface portion 112 which is contiguous with flat surface portion 114 at a predetermined distance from flat surface portion 108, while there is no corresponding portion of conical surface portion 112 at the same distance from flat surface portion 108 on the side of the prong having flat surface portion 116. Thus flat surface portions 114 and 116 render the free end of each prong substantially non-symmetrical about the above-mentioned plane of symmetry of the associated retainer member aperture.

When the free end of a prong is forced into initial portion 88 of a retainer member aperture with the initial angular orientation shown in FIG. 10, non-symmetrical prong surface portions 112a and 112b contact the side surface of aperture portion 88 and act as cam surfaces for applying a twisting force couple or torque to the prong. This force couple or torque acts in a direction which tends to bring flat surface portions 114 and 116 into parallelism with the above-mentioned plane of symmetry of the retainer member aperture. The prong is sufficiently flexible that it responds to this force couple or torque by twisting about its longitudinal axis in the direction indicated by the arrow 118 in FIG. 11 until flat surface portions 114 and 116 are substantially parallel to the plane of symmetry of the retainer member aperture as shown in FIGS. 11 and 12. When this occurs, the free end of the prong can pass freely through initial aperture portion 88 into final aperture portion 90. It should be noted that the retainer member apertures may also stretch outwardly to some degree during twisting of the fastener member prongs. This also facilitates passage of the free end of the prongs through initial aperture portions 88 into final aperture portions 90. The retainer member apertures typically return to their initial size and shape when the associated prongs untwist as described below.

As soon as all of conical surface portion 112 has passed into final aperture portion 90, cam surfaces 112a and 112b lose contact with initial aperture portion 88. The twisting force couple or torque is therefore no longer applied to the prong and the prong untwists in the direction indicated by arrow 120 in FIG. 13 to its initial angular orientation as shown in FIGS. 13 and 14. This permanently interlocks the fastener member and the retainer member by virtue of the overlapping of interlocking surface portions 122 on the fastener member prong and interlocking surface portions 92 in the retainer member aperture. The overlapping of these interlocking surface portions is clearly visible in FIGS. 13 and 14.

More detailed consideration will now be given to the construction and operation of fastener applying cartridge 14. As shown in FIGS. 2 and 3, fastener holding assembly 40 includes an outer housing 60 having a stop member 62 cantilevered from one side into the interior of the housing. U-shaped channel member 64 is disposed in the interior of housing 60 for reciprocal motion parallel to the prongs of fastener members 100. One leg of channel member 64 is located on the proximal side of stop member 62, and the other leg of channel member 64 is located on the distal side of stop member 62. Compression leaf spring 66 is located between stop member 62 and the proximal leg of channel member 64 to resiliently urge channel member 64 in the proximal direction.

Pusher member 68 is fixedly mounted on the distal leg of channel member 64 by means of a dovetail connection between the channel member and the base of the pusher member. As is best seen in FIG. 6, pusher member 68 includes a longitudinal base 70 and a plurality of pusher fingers 72 perpendicular to the base. Each pusher finger 72 extends to the proximal side of the base 102 of a respective one of fastener members 100. Thus pusher fingers 72 are the elements which actually drive fastener members 100 from fastener holding assembly 40 when cartridge 14 is actuated. The bases 54 of pin members 50 are captured between pusher member base 70 and the distal leg of channel member 64. Each channel-shaped portion 56 of each pin member extends through a correspondingly shaped aperture 74 in pusher member base 70 (see also FIG. 7). Channel-shaped portions 56 also extend along the sides of each pusher finger 72 and terminate adjacent the ends of the base 102 of the associated fastener member 100. At the transition between each channel-shaped portion 56 and the associated pin 52, pin member 50 includes a detent 58 for releasably engaging a corresponding detent surface 124 in fastener member 100. The cooperation of detent elements 58 and 124 helps to hold fastener members 100 in fastener holding assembly 40 prior to actuation of that assembly to drive the fastener members.

Leaf spring 42 is mounted on the proximal side of housing 60 adjacent pivot pin 32. The free end of spring 42 (opposite the mounting of spring 42 to housing 60) engages alignment pin 44. Alignment pin 44 extends through the upper portion of housing 60 parallel to the prongs of fastener members 100 and is mounted for longitudinal reciprocation in housing 60. Spring 42 is biased to deflect away from the proximal surface of housing 60 as shown in FIG. 1a so that the free end (not visible) of alignment pin 44 is normally retracted in the proximal direction into housing 60. When the clamp actuating elements 22 and 24 of actuator assembly 12 are positioned as shown in FIG. 1b, however, spring 42 is pressed against the proximal surface of housing 60, thereby driving alignment pin 44 in the distal direction. In this condition the distal end of alignment pin 44 extends from the distal side of housing 60 into an aperture 34 in the end of retainer support member 30 remote from pivot pin 32. In this way alignment pin 44 helps align fastener holding assembly 40 with retainer support member 30 when these two elements are substantially parallel to one another and ready to apply fasteners to tissue clamped between them. When fastener holding assembly 40 is not parallel to retainer support member 30, spring 42 automatically retracts the distal end of alignment pin 44 into housing 60 so that the alignment pin does not interfere with the insertion of tissue in the apparatus or the removal of tissue from the apparatus.

Retainer members 80 are removably retained in apertures in retainer support member 30 by any suitable means such as a light friction fit between the retainer members and the retainer support member, so that after fastener members 100 have been driven through the tissue and into the retainer members, the retainer members will come out of the retainer support member relatively easily.

When the tissue to be fastened has been clamped between the opposing faces of retainer support member 30 and fastener holding assembly 40 and the tissue is to be fastened, pusher actuator member 26 (FIG. 1) is pivoted toward the butt of frame 20 to drive pusher actuator rod 130 (which is part of actuator assembly 12) in the distal direction as shown in FIGS. 4 and 5. The distal end of pusher actuator rod 130 passes through slot 46 in spring 42 and slot 76 in housing 60 and contacts the proximal leg of channel member 64. This causes channel member 64 to translate in the distal direction, thereby compressing compression leaf spring 66 and causing pusher member 68 to also translate in the distal direction. Distal translation of pusher member 68 drives pins 52 and the prongs 104, 106 of fastener members 100 through the tissue and into apertures 84, 86 in retainer members 80. The ends of pins 52 enter apertures 84, 86, but those apertures are large enough adjacent the pins so that the pins are not retained by the retainer members. Pins 52 help prongs 104, 106 penetrate the tissue and reinforce the prongs to help prevent the prongs from buckling. However, pins 52 do not restrain the prongs from twisting as they enter retainer member apertures 84 and 86 as described in detail above.

When pusher actuator rod 130 has completed its driving stroke, the distal leg of channel member 64 is close to stop member 62 as shown in FIGS. 4 and 5. In addition, the free ends of the prongs of all of fastener members 100 are interlocked with the associated retainer members 80 in the manner shown in FIGS. 13 and 14. Fastening of the tissue has now been completed and pivoting actuator member 26 can be released to retract pusher actuator rod 130 in the proximal direction.

As soon as pusher actuator rod 130 retracts, compression leaf spring 66 forces channel member 64 back to its initial position shown in FIGS. 2 and 3. This retracts pins 52 back into housing 60, thereby pulling the pins away from the completed surgical fasteners and also out of the fastened tissue. Thus before the fastened tissue can be removed from the apparatus, pins 52 are automatically retracted by the apparatus in order to avoid any possible injury to the tissue due to contact with the pins during removal of the tissue from the apparatus.

When the fastened tissue is to be removed from the apparatus, pivoting clamp actuator element 22 (FIG. 1) is pivoted out of frame 20 to retract reciprocating element 24. This allows spring 42 to retract alignment pin 44 and also allows fastener holding assembly 40 to pivot away from retainer support member 30. Fastener members 100 have already been released as a result of the retraction of pins 52, and retainer members 80 now pull out of retainer support member 30. The fastened tissue can therefore be removed from the apparatus. Expended fastener applying cartridge 14 is removed from actuator assembly 12 and discarded. The apparatus is ready for reuse when a new cartridge 14 is placed in the actuator assembly.

Although the invention has been illustratively described in the context of a particular embodiment, it will be understood that it is equally applicable to other types of surgical fastening systems. For example, instead of a pivoting fastener applying cartridge 14 as described above, the retainer support member and the fastener holding assembly could be two completely separate cartridge elements which translate linearly relative to one another in a manner analogous to the separate anvil and staple holding assembly in the surgical staplers shown in Green U.S. Pat. No. 3,494,533. The invention is also not limited to applying surgical fasteners in straight rows. For example, the invention is applicable to applying surgical fasteners in annular patterns such as in the circular anastomosis surgical staplers shown in commonly assigned, co-pending Conta et al. U.S. patent application Ser. No. 138,878, filed Apr. 10, 1980. In adapting the invention to that type of apparatus, the retainer support member would again be made entirely separate from the fastener holding assembly in a manner analogous to the separate anvil and staple holding assembly in the Conta et al. apparatus.

The invention is also not limited to fastener applying apparatus in which the fastener applying portion is made as a disposable cartridge which is separate from a permanent actuator assembly. The fastener applying portion could be made integral with the actuator assembly and the entire apparatus could be made disposable after a single use.

Plastic-like materials that are suitable for use as absorbable or biodegradable surgical fasteners include cat gut (collagen derived from sheep intestinal submucosa), polyglycolic acid, polylactic acid, copolymer blends of polyglycolic and polylactic acid, reconstituted collagen, polyesters, polyamino acids such as casein, albumin and the like, polyhydric alcohol polymers such as polyvinyl alcohol, cellulose glycolic acid ethers and esters of alpha-cyanoacrylic acid such as methyl alpha-cyanoacrylate. Polyglycolic acid is disclosed in U.S. Pat. Nos. 3,463,158; 3,739,773; and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841; 3,564,078; and 3,759,264. In a preferred embodiment, the fasteners of this invention are made by injection molding an absorbable amorphous copolymer of 10–50% (by weight) glycolide and 50–90% lactide. The molecular weight of the copolymer should be from about 30,000–40,000 up to about 130,000. The foregoing are merely illustrative of suitable biologically absorbable plastic-like materials. Other suitable absorbable plastic-like fastener materials (e.g., polymers of p-dioxanone) will be apparent to those skilled in the art. Examples of suitable non-absorbable plastic-like materials are polyethylene, polypropylene, and nylon.

It will be understood that the embodiments shown and described herein are only illustrative of the principles of the invention, and that various modifications can be made by those skilled in the art without departing from the scope and spirit of the invention. For example, the surgical fasteners of this invention can be used in several different types of fastener applying devices, several examples of which are described above.

I claim:

1. A surgical fastener of plastic-like material comprising:
    a fastener member including a base and at least two spaced substantially parallel prongs extending substantially perpendicularly from the base; and
    a retainer member including at least two apertures, each aperture being adapted to receive and retain the free end of a respective one of the prongs, each aperture including (a) cam surface means for contacting the associated prong and causing it to twist about its longitudinal axis as it initially enters the aperture and then allowing the prong to untwist after the prong has penetrated a predetermined distance into the aperture and (b) interlocking surface means for interlockingly engaging the associated prong to prevent withdrawal of the prong from the aperture after the prong has been allowed to untwist by the cam surface means.

2. The apparatus defined in claim 1 wherein each prong includes a first side surface portion parallel to which and contiguous with which a respective metal pin is disposed during application of the fastener member to the body tissue to be fastened, the metal pins facilitating passage of the prongs through the body tissue, and wherein the remaining portion of the side surface of each prong includes cam surface portions and interlocking surface portions, the cam surface portions cooperating with the cam surface means of the associated retainer member aperture to cause the prong to twist, and the interlocking surface portions interlocking with the interlocking surface means of the associated retainer member aperture when the prong untwists.

3. A surgical fastener of plastic-like material comprising:
    a fastener member including a longitudinal base and at least two spaced mutually parallel prongs extending from the base substantially perpendicular to the longitudinal axis of the base; and
    a longitudinal retainer member having at least two apertures, each aperture being adapted to receive and interlockingly engage the free end of a respective one of the prongs to secure the fastener member and the retainer member together, the initial portion of each aperture which the associated prong first enters being too small to pass the free end of the prong in the initial angular orientation of the prong about its longitudinal axis, and the free end of the prong and the initial portion of the aperture having cooperating cam surfaces for causing the free end of the prong to twist about its longitudinal axis to an angular orientation in which it can pass through the initial portion of the aperture, after which the free end of the prong resumes its initial angular orientation and interlocks with the retainer member.

4. The apparatus defined in claim 3 wherein each prong includes a first side surface portion parallel to which and contiguous with which a respective metal pin is disposed during application of the fastener member to the body tissue to be fastened, the metal pins facilitating passage of the prongs through the body tissue, and wherein the remaining portion of the side surface of each prong includes cam surface portions and interlocking surface portions, the cam surface portions cooperating with the cam surfaces of the retainer member aperture to cause the free end of the prong to twist, and the interlocking surface portions interlocking with the associated retainer member aperture when the prong resumes its initial angular orientation.

5. A surgical fastener of plastic-like material comprising:
 a fastener member including a longitudinal base and at least two spaced mutually parallel prongs extending from the base substantially perpendicular to the longitudinal axis of the base; and
 a retainer member having at least two apertures, each aperture being adapted to receive the free end of a respective one of the prongs, the free end of each prong being shaped so that it will not pass through an initial portion of the associated aperture in the normal angular orientation of the prong about its longitudinal axis but so that it will pass through the initial portion of the aperture in a second angular orientation which is displaced from the normal angular orientation, the free end of each prong and the associated aperture having cooperating cam surfaces for twisting the prong from the normal angular orientation to the second angular orientation when the prong is forced into the aperture, the free end of the prong then passing through the initial portion of the aperture, returning to its normal angular orientation, and being thereby permanently retained in the aperture.

6. The apparatus defined in claim 5 wherein each prong includes a first side surface portion parallel to which and contiguous with which a respective metal pin is disposed during application of the fastener member to the body tissue to be fastened, the metal pins facilitating passage of the prongs through the body tissue, and wherein the remaining portion of the side surface of each prong includes cam surface portions and interlocking surface portions, the cam surface portions cooperating with the cam surfaces of the retainer member aperture to twist the prong from the normal angular orientation to the second angular orientation, and the interlocking surface portion interlocking with the associated retainer member aperture when the prong returns to its normal angular orientation.

7. A surgical fastener of plastic-like material comprising:
 a fastener member including a longitudinal base and at least two spaced mutually parallel prongs extending from the base substantially perpendicular to the longitudinal axis of the base;
 a retainer member having at least two apertures, each aperture being adapted to receive the free end of a respective one of the prongs;
 each prong and the associated aperture including mutually interlocking surface portions which when engaged permanently retain the free end of the prong in the aperture; and
 each prong and the associated aperture including cam surface portions which cooperate with one another when the free end of the prong is introduced into the aperture to initially twist the prong about its longitudinal axis so that the interlocking surface portions bypass one another, after which the cam surfaces disengage, thereby allowing the prong to untwist and causing the interlocking surface portions to engage.

8. The surgical fastener defined in claim 7 wherein each prong includes a first side surface portion parallel to which and contiguous with which a respective metal pin is disposed during application of the fastener member to the body tissue to be fastened, the metal pins facilitating passage of the prongs through the body tissue, and wherein the remaining portion of the side surface of each prong includes the cam surface portions and the interlocking surface portions of the prong.

9. Apparatus for applying a surgical fastener to body tissue comprising:
 a fastener holding assembly containing at least one fastener member including a longitudinal base and at least two spaced substantially parallel prongs extending from the base perpendicular to the longitudinal axis of the base;
 a retainer support member removably containing at least one retainer member including at least two apertures, each aperture being adapted to receive and retain the free end of a respective one of the prongs;
 pusher means associated with the fastener holding assembly for pushing the fastener member from the fastener holding assembly so that the prongs pass through body tissue disposed between the fastener holding assembly and the retainer support member and so that the free ends of the prongs enter and are retained by the retainer member apertures to fasten the tissue, the pusher means including a metal pin substantially parallel to and contiguous with each prong, each pin extending beyond the free end of the associated prong and traveling with the prong during the pushing of the fastener member to facilitate the passage of the associated prong through the tissue; and
 means associated with the fastener member holding assembly for automatically retracting the pins into the fastener holding assembly when the fastener holding assembly is moved away from the fastened tissue.

10. The apparatus defined in claim 9 wherein the fastener holding assembly is pivotally mounted adjacent one end of the retainer support member.

11. The apparatus defined in claim 9 wherein each aperture includes cam surface means for causing the associated prong to twist about its longitudinal axis as it initially enters the aperture and for allowing the prong to untwist to interlock with the aperture after the prong has penetrated a predetermined distance into the aperture.

12. The apparatus defined in claim 11 wherein each pin is adjacent a first portion of the side surface of the associated prong and wherein the remaining portion of the side surface of the prong includes cam surface portions and interlocking surface portions, the cam surface portions cooperating with the associated retainer member aperture to cause the prong to twist, and the interlocking surface portions interlocking with the retainer member aperture when the cam surface portions allow the prong to untwist.

13. The apparatus defined in claim 12 wherein each pin and the associated prong include cooperating detent means for retaining the fastener member in the fastener holding assembly prior to operation of the pusher means.

14. The apparatus defined in claim 9 wherein the fastener member and the retainer member are made of plastic-like material.

15. The apparatus defined in claim 14 wherein each prong includes (1) a first side surface portion with which the associated pin is parallel and contiguous during application of the fastener member and (2) a second side surface portion including an interlocking surface portion, and wherein each retainer member aperture includes an interlocking surface portion for interlockingly engaging the interlocking surface portion of the associated prong when the prong is inserted in the aperture.

16. The apparatus defined in claim 15 wherein the second side surface portion of each prong further includes a cam surface portion for contacting the retainer member as the prong enters the aperture and before the interlocking surface portions interlockingly engage, said contact causing the prong to momentarily deflect, after which deflection the interlocking surface portions interlockingly engage.

17. The apparatus defined in claim 9 wherein each fastener member includes two prongs, and wherein the two pins associated with each fastener member are the two parallel legs of a U-shaped pin structure having a base substantially parallel to the base of the fastener member.

18. The apparatus defined in claim 17 wherein the base of the pin structure is spaced from the base of the associated fastener member and is disposed on the side of the associated fastener member base which is remote from the associated retainer member, and wherein the pusher means includes a pusher member associated with each fastener member and disposed between the fastener member base and the associated pin structure base, the pusher member having two parallel spaced sides which are respectively contiguous with portions of the legs of the associated pin structure.

19. Apparatus for applying a surgical fastener to body tissue comprising:
   a fastener holding assembly containing at least one fastener member including a longitudinal base and at least two spaced substantially parallel prongs extending from the base perpendicular to the longitudinal axis of the base;
   a retainer support member removably containing at least one retainer member including at least two apertures, each aperture being adapted to receive and retain the free end of a respective one of the prongs, each aperture causing the associated prong to twist about its longitudinal axis as it initially enters the aperture and then allowing the prong to untwist to interlock with the aperture;
   pusher means associated with the fastener holding assembly for pushing the fastener member from the fastener holding assembly so that the prongs pass through body tissue disposed between the fastener holding assembly and the retainer support member and so that the free ends of the prongs enter and interlock with the retainer member apertures to fasten the tissue, the pusher means including a metal pin substantially parallel to and contiguous with each prong, each pin extending beyond the free end of the associated prong and traveling with the prong during the pushing of the fastener member to facilitate the passage of the associated prong through the tissue, the pins permitting twisting of the prongs as is required to interlock the fastener member and the retainer member, and the pins being retractable from the fastener member after the fastener member and retainer member interlock.

20. The apparatus defined in claim 19 wherein the fastener holding assembly is pivotally mounted adjacent one end of the retainer support member.

21. The apparatus defined in claim 19 wherein the fastener holding assembly further includes means for automatically retracting the pins into the fastener holding assembly when the fastener holding assembly is moved away from the fastened tissue.

22. The apparatus defined in claim 19 wherein each pin is adjacent a first portion of the side surface of the associated prong and wherein the remaining portion of the side surface of the prong includes cam surface portions and interlocking surface portions, the cam surface portions cooperating with the associated retainer member aperture to cause the prong to twist, and the interlocking surface portions interlocking with the retainer member aperture when the cam surface portions allow the prong to untwist.

23. The apparatus defined in claim 22 wherein each pin and the associated prong include cooperating detent means for retaining the fastener member in the fastener holding assembly prior to operation of the pusher means.

* * * * *

UNITED STATES PATENT AND TRADEMARK OFFICE
CERTIFICATE OF CORRECTION

PATENT NO. : 4,402,445
DATED : September 6, 1983
INVENTOR(S) : David T. Green

It is certified that error appears in the above—identified patent and that said Letters Patent is hereby corrected as shown below:

| Column | Line | |
|--------|------|---|
| 3 | 51 | after "mechanism" insert --including-- |

Signed and Sealed this

Twenty-sixth Day of February 1985

[SEAL]

Attest:

DONALD J. QUIGG

Attesting Officer  Acting Commissioner of Patents and Trademarks